(12) United States Patent
Simpson et al.

(10) Patent No.: US 9,119,802 B2
(45) Date of Patent: Sep. 1, 2015

(54) E. COLI LPFA ANTIGEN FOR PREVENTION AND TREATMENT OF INFECTIOUS DISEASES

(75) Inventors: Kenneth W. Simpson, Ithaca, NY (US); Belgin Dogan, Ithaca, NY (US)

(73) Assignee: Cornell University, ithaca, NY (US)

( * ) Notice: Subject to any disclaimer, the term of this patent is extended or adjusted under 35 U.S.C. 154(b) by 133 days.

(21) Appl. No.: 13/318,590

(22) PCT Filed: May 4, 2010

(86) PCT No.: PCT/US2010/033585
§ 371 (c)(1),
(2), (4) Date: Oct. 11, 2012

(87) PCT Pub. No.: WO2010/129578
PCT Pub. Date: Nov. 11, 2010

(65) Prior Publication Data
US 2013/0022664 A1    Jan. 24, 2013

Related U.S. Application Data

(60) Provisional application No. 61/175,872, filed on May 6, 2009.

(51) Int. Cl.
| | | |
|---|---|---|
| A61K 38/00 | (2006.01) | |
| A61K 38/16 | (2006.01) | |
| A61K 39/00 | (2006.01) | |
| C07K 14/245 | (2006.01) | |
| A61K 39/108 | (2006.01) | |
| G01N 33/569 | (2006.01) | |

(52) U.S. Cl.
CPC ...... *A61K 39/0258* (2013.01); *G01N 33/56916* (2013.01); *G01N 2333/245* (2013.01); *G01N 2800/065* (2013.01)

(58) Field of Classification Search
CPC .................. A61K 39/0258; A61K 2039/522; A61K 35/74; A61K 39/00; C12Q 1/689; C12Q 1/00; G01N 2333/245; G01N 2800/065; G01N 33/56916; C07K 14/245
USPC .......... 424/150.1, 190.1, 184.1, 242.1, 257.1, 424/241.1; 435/6.15, 7.37
See application file for complete search history.

(56) References Cited

U.S. PATENT DOCUMENTS

| | | | |
|---|---|---|---|
| 2005/0288866 A1* | 12/2005 | Sachdeva et al. ............... | 702/19 |
| 2006/0083716 A1 | 4/2006 | Kaufman et al. | |
| 2008/0193470 A1 | 8/2008 | Masignani et al. | |
| 2008/0274131 A1 | 11/2008 | Renner et al. | |
| 2008/0286310 A1 | 11/2008 | Zhu et al. | |

FOREIGN PATENT DOCUMENTS

WO     WO 2006089264 A2 *   8/2006

OTHER PUBLICATIONS

Doughty et al. 2002 (Identification of a novel fimbrial gene cluster related to long polar fimbriae in locus of enterocyte effacement-negative strains of Enterohemorrhagic *Escherichia coli*. Infection and Immunity; 2002: 6761-6769).*
Kaper et al. 2004 (Pathogenic *Escherichia coli*; Nature Reviews Microbiology; 2:123-140).*
Touchon et al. 2009 (Organised genome dynamics in the *Escherichia coli* species results in highly diverse adaptive paths; PLoS Genetics 5(1): 1-25; published Jan. 2009).*
Humphries, et al., *Salmonella enterica* Serotype *typhimurium* Fimbrial. Infect Immun, Sep. 2005, vol. 73, No. 9, pp. 5329-5338; abstract.
International Preliminary Report on Patentability of PCT/US2010/033585, Sep. 14, 2010.
International Search Report of PCT/US10/33585, Sep. 14, 2010.
Norris, et al., Expression and Transcriptional Control of the *Salmonella typhimirium* LPF Fimbrial Operon by Phase Variation, Molecular Microbiology. Jul. 1998. vol. 29, No. 1, pp. 311-320.
UniProt entry B3H9Y6. Uniprot. Feb. 10, 2009 [online].[Retrieved on Jun. 21, 2010]. Retrieved from the internet <URL:http://www.uniprot.org/uniprot/B3H976.txt?version=4>, p. 1, line SQ.

* cited by examiner

*Primary Examiner* — Gary Nickol
*Assistant Examiner* — Mary Lyons
(74) *Attorney, Agent, or Firm* — Foley & Lardner LLP

(57) ABSTRACT

The present disclosure relates to methods and compositions for the treatment and prevention of microbial infections and for the enhancement of resistance to infection. The disclosure includes administration of an effective amount of an *E. coli* LpfA antigen to enhance the immune system to prevent infections that cause, e.g., inflammatory bowel diseases, bovine mastitis and metritis. The disclosure also includes methods for diagnosing microbial infection and conditions associated with microbial infection by detecting an *E. coli* LpfA polypeptide or nucleic acid.

14 Claims, 4 Drawing Sheets

E. COLI LPFA ANTIGEN FOR PREVENTION AND TREATMENT OF INFECTIOUS DISEASES

STATEMENT OF GOVERNMENT SUPPORT

The invention was made with United States government support awarded by the following agencies: NIH K08 DK002938. The United States government has certain rights in this invention.

CROSS-REFERENCE TO RELATED APPLICATIONS

The present application is the U.S. National Stage application of International Application No. PCT/US2010/033585, filed on May 4, 2010, which claims priority to U.S. Provisional Patent Application Ser. No. 61/175,872, filed on May 6, 2009, the entire contents of which are hereby incorporated by reference in their entirety.

TECHNICAL FIELD

The present disclosure relates generally to therapeutic compositions useful in the treatment and/or prevention of disease. The disclosure also relates to methods of diagnosing a microbial infection and associated diseases by detecting nucleic acids and polypeptides associated with E. coli virulence.

BACKGROUND

The following description is provided to assist the understanding of the reader. None of the information provided or references cited is admitted to be prior art to the present technology.

Infection by pathogenic organisms is one of the major causes of chronic and acute disease. In particular, infection resulting from microbial sources—such as bacteria, viruses and protozoans—continue to claim millions of lives worldwide. With microbial species increasingly becoming resistant to conventional antibiotics, it would be desirable to provide alternative and preferably prophylactic means of protecting against and fighting microbial infection. For example, intestinal bacteria are implicated increasingly as a pivotal factor in the development of Crohn's disease, but the specific components of the complex polymicrobial enteric environment driving the inflammatory response are unresolved.

E. coli infections are not uncommon in other organs or species. In particular, coliform infections have been identified in an ever increasing proportion of mastitis cases and infections of the female genital tract are often observed, and have inspired research into the pathogenesis of persistent E. coli infections. There is still debate about the precise mechanisms involved in the persistence of these infections, but it is clear that adhesion to epithelial cells and subsequent invasion of epithelial cells, together with prolonged intracellular survival of the bacteria play an important role in persistence of infection.

SUMMARY

This invention relates generally to the long polar fimbriae subunit A (LpfA) of E. coli and uses of the same. In particular, the present disclosure relates to the preparation of vaccines that stimulate an immune response against cells expressing a LpfA antigen to provide a prophylactic and/or therapeutic benefit. The disclosure also relates to the detection of LpfA variants for the diagnosis of infectious diseases in animal subject. In further embodiments, the present disclosure provides methods to stimulate the mucosal immune system by using LpfA as a means of specifically targeting Peyer's patches which are found in the ileum and function to facilitate the generation of the immune response.

In one aspect, the present disclosure provides a composition comprising an immunologically effective amount of an E. coli LpfA antigen and a pharmaceutically acceptable carrier, wherein the LpfA antigen is a polypeptide of SEQ ID NO: 2 or SEQ ID NO: 4. In one embodiment, the disclosure further comprises an adjuvant.

In one aspect, the present disclosure provides a method of eliciting an immune response in an animal subject, the method comprising administering to the subject an immunologically effective amount of an E. coli LpfA antigen and a pharmaceutically acceptable carrier, wherein the LpfA antigen is a polypeptide of SEQ ID NO: 2 or SEQ ID NO: 4. In one embodiment, the immune response provides prophylaxis against a microbial infection caused by a pathogenic E. coli. In one embodiment, the microbial infection results in a condition selected from the group consisting of: Crohn's disease, mastitis and metritis. In one embodiment, the administering is oral, intradermal, intramuscular, intraperitoneal, intravenous, subcutaneous, or intranasal.

In another aspect, the present disclosure provides a method for diagnosing an infectious disease in a mammalian subject, the method comprising: (a) providing a sample from the subject; and (b) detecting the presence of a LpfA 154 variant, a Lpf 141 variant, or both a LpfA 154 and LpfA 141 variant, if present, in the sample, wherein the presence of a LpfA 154 variant, a Lpf 141 variant, or both a LpfA 154 and LpfA 141 variant in the sample indicates a diagnosis of a microbial infection or associated condition in the subject.

In one embodiment, the LpfA 154 variant comprises SEQ ID NO: 1. In one embodiment, the LpfA 141 variant comprises SEQ ID NO: 3. In one embodiment, the microbial infection or associated condition is ileitis. In one embodiment, the microbial infection or associated condition is Crohn's disease. In one embodiment, the sample is an ileal biopsy sample. In one embodiment, wherein the subject is a human. In one embodiment, the microbial infection or associated condition is bovine mastitis. In one embodiment, the sample is a milk sample. In one embodiment, the microbial infection or associated condition is bovine metritis. In one embodiment, the detecting is by PCR.

In another aspect, the present disclosure provides a composition comprising a purified LpfA polypeptide of SEQ ID NO: 2 or SEQ ID NO: 4 and a carrier entity associated with a bioactive agent, wherein the polypeptide is covalently or non-covalently bound to a carrier entity. In one embodiment, the carrier entity is selected from the group consisting of a nanoparticle, a microparticle, a liposome, a bacteria, a phage and a viral carrier. In one embodiment, the carrier entity is a nanoparticle, microparticle, or liposome and the nanoparticle, microparticle, or liposome is loaded with the bioactive agent or encapsulated with the bioactive agent. In one embodiment, the bioactive agent is a vaccine.

In another aspect, the present disclosure provides a method of administering a bioactive agent to a subject having intestinal epithelium, the method comprising contacting the intestinal epithelium with a composition comprising a purified LpfA polypeptide of SEQ ID NO: 2 or SEQ ID NO: 4 and a carrier entity associated with a bioactive agent, wherein the polypeptide is covalently or non-covalently bound to a carrier entity. In one embodiment, the subject is a mammal. In one embodiment, the mammal is a human. In one embodiment, the administration is via the oral, rectal, subcutaneous, intramuscular, nasal, or intravenous route.

In one aspect, the present disclosure provides an isolated nucleic acid and vectors comprising a sequence of SEQ ID NO: 1 or SEQ ID NO: 3. In one embodiment, the vectors further comprise a promoter operably-linked to the nucleic acid molecule. The disclosure also provides a host cell comprising the vector.

DETAILED DESCRIPTION

Figure 1:
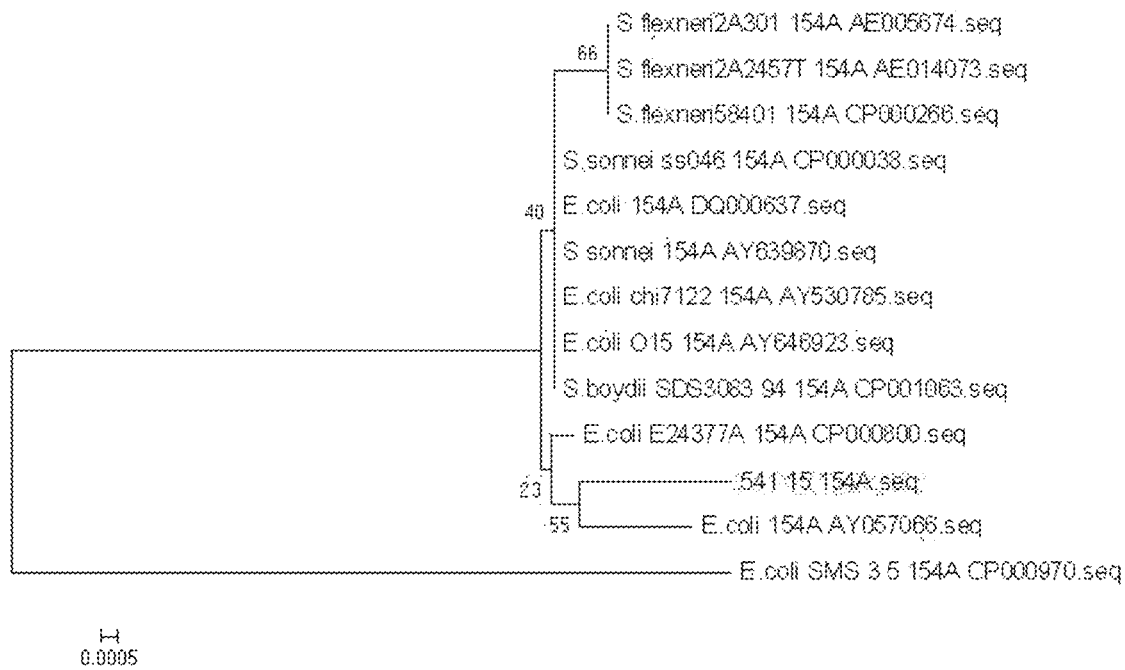
FIG. 1 is a dendrogram showing the alignment of the LpfA subunit present in Crohn's ileitis-associated strain 541-15.

It is to be appreciated that certain aspects, modes, embodiments, variations and features of the invention are described below in various levels of detail in order to provide a substantial understanding of the present invention. Unless defined otherwise, all technical and scientific terms used herein generally have the same meaning as commonly understood by one of ordinary skill in the art to which this invention belongs. As used in this specification and the appended claims, the singular forms "a", "an" and "the" include plural referents unless the content clearly dictates otherwise. For example, reference to "a polypeptide" includes a combination of two or more polypeptides, and the like.

As used herein, the "administration" of a vaccine, agent or drug to a subject or cell includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen". Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to produce polypeptides which elicit the desired immune response.

As used herein, the term "biological sample" means sample material derived from or contacted by living cells. The term "biological sample" is intended to include tissues, cells and biological fluids isolated from a subject, as well as tissues, cells and fluids present within a subject. Biological samples of the invention include, e.g., but are not limited to, whole blood, plasma, semen, saliva, tears, urine, fecal material, sweat, buccal, skin, cerebrospinal fluid, milk, and hair. Biological samples can also be obtained from biopsies of internal organs, such as a biopsy of ileum tissue. Biological samples can be obtained from subjects for diagnosis or research, or can be obtained from undiseased individuals as controls or for basic research.

As used herein, the term "carrier entity" refers to a nanoparticle, microparticle, droplet, liposome bacterium, phage or virus, etc. that can carry a bioactive agent. As used herein, the term "carrier entity" also refers to a bacterium, phage or virus that can encode a bioactive agent.

As used herein, the terms "diagnose" or "diagnosis" or "diagnosing" refer to distinguishing or identifying a disease, syndrome or condition or identifying a person having a particular disease, syndrome or condition. In illustrative embodiments, assays are used to diagnose a microbial infection, or a condition associated with a microbial infection, such as Crohn's disease, mastitis, or metritis.

As used herein, the term "effective amount" or "pharmaceutically effective amount" or "therapeutically effective amount" of a composition, is a quantity sufficient to achieve a desired biological effect, e.g., treatment or prophylaxis against a microbial infection. Typically, the biological effect is measured in comparison to an animal not administered the composition. The amount of a composition of the invention administered to the animal will depend on such factors as general health, age, sex, body weight and tolerance to the composition. The skilled artisan will be able to determine appropriate dosages depending on these and other factors. The compositions can also be administered in combination with one or more additional agents known in the art, e.g., antibiotics.

As used herein, the terms "identical" or "percent identity", when used in the context of two or more nucleic acids or polypeptide sequences, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region) when compared and aligned for maximum correspondence over a comparison window or designated region as measured using a BLAST or BLAST 2.0 sequence comparison algorithms with default parameters described below, or by manual alignment and visual inspection (see, e.g., NCBI web site). This term also refers to, or can be applied to, the complement of a test sequence. The term also includes sequences that have deletions and/or additions, as well as those that have substitutions.

As used herein, the term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the animal body of invading pathogens, cells or tissues infected with pathogens.

As used herein, "immunogen" refers to a substance that is able to stimulate or induce a humoral antibody and/or cell-mediated immune response in a mammal.

The term "isolated" as used herein with respect to a nucleic acid, including DNA and RNA, refers to nucleic acid molecules that are substantially separated from other macromolecules normally associated with the nucleic acid in its natural state. An isolated nucleic acid molecule is substantially separated from the cellular material normally associated with it in a cell or, as relevant, can be substantially separated from bacterial or viral material; or from culture medium when produced by recombinant DNA techniques; or from chemical precursors or other chemicals when the nucleic acid is chemically synthesized. In general, an isolated nucleic acid molecule is at least about 50% enriched with respect to its natural state, and generally is about 70% to about 80% enriched, particularly about 90% or 95% or more. In suitable embodiments, an isolated nucleic acid constitutes at least about 50% of a sample containing the nucleic acid, and can be at least about 70% or 80% of the material in a sample, particularly at least about 90% to 95% or greater of the sample. An isolated nucleic acid can be a nucleic acid fragment that does not occur in nature and, therefore, is not found in a natural state.

The term "isolated" also is used herein to refer to polypeptides that are substantially separated from other macromolecules normally associated with the polypeptide in its natural state. An isolated polypeptide can be identified based on its being enriched with respect to materials it naturally is associated with or its constituting a fraction of a sample containing the polypeptide to the same degree as defined above for an "isolated" nucleic acid, i.e., enriched at least about 50% with respect to its natural state or constituting at least about 50% of a sample containing the polypeptide. An isolated polypeptide, for example, can be purified from a cell that normally expresses the polypeptide or can be produced using recombinant DNA methodology.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature. In a particular embodiment, the polypeptide is an *E. coli* LpfA polypeptide or a subsequence or variant thereof.

As used herein, the term "substitution" refers to variants that have at least one amino acid residue in the LpfA polypeptide or a fragment thereof replaced by a different residue. Conservative substitutions typically include the substitution of one amino acid for another with similar characteristics such as hydrophobic, polar, acidic or basic side chains. Conservative substitution tables providing functionally similar amino acids are well known in the art. For example, the following six groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E); Polar: Serine (S), Threonine (T), Asparagine (N), Glutamine (Q).

As used herein, the term "subject" refers to an organism, such as a mammal, e.g., a human, but can also be an animal such as a domestic animal (e.g., dogs, cats and the like), farm animal (e.g., cows, sheep, pigs, horses and the like) or laboratory animal (e.g., monkey, rats, mice, rabbits, guinea pigs and the like).

As used herein, the terms "treating," "treatment" and "alleviation" refer to both therapeutic treatment and prophylactic or preventative measures, wherein the object is to prevent or slow down (lessen) the targeted pathologic condition or disorder. A subject is successfully "treated" for a disorder if the subject shows observable and/or measurable reduction in or absence of one or more signs and symptoms of a particular disease or condition.

The term "vaccine" as used herein is defined as a material used to provoke an immune response after administration of the material to a mammal.

As used herein, the term "variant" refers to a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be naturally occurring such as an allelic variant, or can be a variant that is not known to occur naturally. Non-naturally occurring variants of nucleic acids and peptides may be made by mutagenesis techniques or by direct synthesis.

Overview

The present invention is based on the discovery that LpfA is a prevalent virulence factor in ileal-associated *E. coli*, as well as *E. coli* that is associated with mastitis and metritis in cattle. More generally, LpfA may be an important factor in a variety of diseases associated with pathogenic *E. coli*. These genes are substantially different to many previously sequenced LpfA genes. Genes encoding LpfA in ileal-derived *E. coli* fall into two broad categories/variants, distinguished in part by the position of the LpfA operon in *E. coli*—141 and 154: (1) those with homology to LpfA141; and (2) those with homology to LpfA 154. The present inventors discovered that *E. coli* strains containing sequences encoding LpfA are more invasive in cultured epithelial cells than strains lacking these virulence determinants. Deletion of LpfA in *E. coli* strains impairs their ability to translocate across co-cultured M cells and CACO-2 epithelial cells. LpfA was also identified as an important factor for trafficking *E. coli* across Peyer's patches.

Accordingly, the disclosure relates inter alia to immunogenic compositions and methods for the prevention and treatment of diseases, such as microbial infections. The disclosure also relates to methods for detecting and diagnosing microbial infection using the inventive polypeptides and polynucleotides. The disclosure also relates to LpfA polypeptides as targeting moieties for delivery of a bioactive agent to Peyer's patches. Each of these aspects will be discussed in the following sections.

Immunogenic Compositions and Related Methods

In one aspect, the present disclosure provides immunogenic compositions and methods of eliciting an immune response in a host comprising administering an effective amount of an immunogenic composition. The immunogenic composition may be used prophylactically as part of a vaccination system in which the composition is administered prior to infection, or in the treatment of a particular infection. The immune response may be a humoral or a cell-mediated immune response. Immunogenicity may be improved by the co-administration of antigens with adjuvants. Adjuvants may act by retaining the antigen locally near the site of administration facilitating a slow sustained release of antigen to cells. Adjuvants can also attract immune cells to the site of injection and stimulate such cells to elicit immune responses. A wide range of adjuvants can aid in evoking an immune response. These include, but are not limited to, pluronic polymers with mineral oil, Freund's complete adjuvant, lipid A, liposomes and cholera toxin subunit B or its genetically modified variants.

In one aspect, the present disclosure provides immunogens that are LpfA polypeptides or peptide fragments or variants thereof. As used herein, the term "LpfA polypeptide" refers to an immunologically active fragment of a LpfA polypeptide. In some embodiments, a peptide fragment may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39 amino acids in length.

The immunogens may also be variant LpfA polypeptides where residues have been altered with respect to the native sequence. For example, it may be desirable to improve the biological properties of the peptides, such as immunogenicity. In some embodiments, variant LpfA polypeptides differ from the native sequence by 1, 2, 3, 4, 5, 6, 7, 8, 9, 10, 11, 12, 15, or amino acids. Such modifications include, for example, deletions from, and/or insertions into and/or substitutions of, residues within the amino acid sequences of the LpfA polypeptides. Any combination of deletion, insertion, and substitution is made to obtain the LpfA polypeptide of interest, as long as the obtained peptide possesses the desired properties, i.e., immunogenicity. In some embodiments, the LpfA polypeptide has at least 75%, at least 80%, at least 85%, at least 90%, at least 95%, at least 97% sequence identity to the corresponding fragment from the native LpfA polypeptide. Amino acid sequence variants of LpfA polypeptides may be prepared by introducing appropriate nucleotide changes into the nucleic acid encoding the peptide, or by peptide synthesis.

In particular embodiments, the LpfA polypeptide immunogens have a sequence according to any one of SEQ ID NOs: 2 or 4 shown in Tables 2 and 4, respectively, or variants thereof having 1, 2, or 3 amino acid substitutions, deletions, or insertions. The LpfA polypeptide immunogens of SEQ ID NOs: 2 and 4 may be encoded by the nucleotide sequences of SEQ ID NO: 1 and 3, respectively.

TABLE 1

Nucleotide Sequence of LpfA 154 Variant (SEQ ID NO: 1)
ATGAAGCGTAATATTATAGGCGGTGCATTCACTCTGGCATCTCTAATGC

TGGCCGGGCATGCACTGGCAGAAGATGGTGTTGTTCACTTCGTCGGTGA

AATTGTCGACACTACTTGTGAAGTTACCTCCGATACAGCCGATCAAATT

GTCCCACTGGGTAAAGTCAGTAAAAATGCATTTTCAGGTGTAGGTAGTC

TGGCGTCGCCACAGAAGTTCAGTATTAAGCTTGAAAATTGCCCGGCAAC

GTACACTCAAGCAGCCGTTCGTTTTGATGGTACAGAAGCGCCTGGCGGC

GACGGCGACCTGAAAGTGGGTACGCCGCTTACAGCAGGCAACCCTGGTG

ATTTTACCGGTACAGGACAAGCGATTGCGGCAACCGGCGTTGGTATTCG

TATTTTTAACCAGTCCGATAATTCGCAGGTTAAACTTTATAACGACTCT

TABLE 1-continued

Nucleotide Sequence of LpfA 154 Variant

GCTTATACCGCTATCGATGCTGAAGGCAAGGCTGAAATGAAGTTTATTG

CACGCTATGTGGCAACCAATGCGACCGTAACGGCTGGTACGGCGAACGC

GGATTCACAATTTACTGTCGAATATAAGAAA

TABLE 2

Polypeptide Sequence of LpfA 154 Variant (SEQ ID NO: 2)
MKRNIIGGAFTLASLMLAGHALAEDGVVHFVGEIVDTTCEVTSDTADQI

VPLGKVSKNAFSGVGSLASPQKFSIKLENCPATYTQAAVRFDGTEAPGG

DGDLKVGTPLTAGNPGDFTGTGQAIAATGVGIRIFNQSDNSQVKLYNDS

AYTAIDAEGKAEMKFIARYVATNATVTAGTANADSQFTVEYKK

TABLE 3

Nucleotide Sequence of LpfA 141 Variant (SEQ ID NO: 3)
ATGAAAAAGGTTCTGTTTGCCTTATCTGCGCTTGCGCTGACCTCTACTT

CCGTATTCGCAGCTGATGCAGGCGACGGTTCTGTTAAATTCACCGGAGA

GATTGTTGACGCCGCTTGTGTTGTGTCTCCAGACACTCAAAAACAAGAA

GTTGTTCTGGGCCAGGTGAACAAGTCTGTGTTTACCACTACTGGTGATA

AATCTGCAGCAACTCCGTTCAAAATTAAACTGGAAAACTGCGATATCTC

CACTTTCAAAAATGTGGAGATCAGCTTTAACGGTGTTGGCGACGCAGAC

AACAGCAAACTGATTTCTGTAAGCACTGAACCAGGTGCCGCAACTGGCG

TGGGTATTGGTATTTATGATAATACCAATACGCTGGTTGATCTGAATAC

CGGTAAATCTGCTACCGTCCTGAAAGAAGGCCAGACTGTTCTGTATTTT

ACCGCTAACTATGTCGCTACCAAAAATGCAGTAACCATCGGTTACGGTA

ATGCCGAAGTCGACTTCAACCTGACTTACAACTAA

TABLE 4

Polypeptide Sequence of LpfA 141 Variant (SEQ ID NO: 4)
MKKVLFALSALALTSTSVFAADAGDGSVKFTGEIVDAACVVSPDTQKQE

VVLGQVNKSVFTTTGDKSAATPFKIKLENCDISTFKNVEISFNGVGDAD

NSKLISVSTEPGAATGVGIGIYDNTNTLVDLNTGKSATVLKEGQTVLYF

TANYVATKNAVTIGYGNAEVDFNLTYN

A peptide segment can be chemically synthesized which corresponds precisely with the amino acid sequence of the region of interest of the LpfA polypeptide being studied and the peptide may be coupled to a carrier protein and injected into a suitable host to obtain antibodies. Peptides may be synthesized according to any methods known in the art. For example, Fmoc synthesis technology may be used for the synthesis. Wang Fmoc resins are added into the synthesis well. After de-protection (removing the Fmoc protection group), an Fmoc amino acid is coupled onto the resins. The resins are then de-protected again before adding the next Fmoc amino acid. The process is repeated according to the desired peptide sequence until the last amino acid is coupled. After all amino acids are coupled onto the resins, the peptides are de-protected to remove Fmoc and any other protected side group. The peptides are then cleaved off from the resins, precipitated with ether, washed, and dried. The purification of peptides may be performed using a preparative HPLC and the MW of the peptide may be measured on a mass spectrometer.

In one aspect, the present disclosure provides methods for the prevention or treatment of a microbial infection by administering an effective amount of LpfA polypeptide sufficient to elicit an immune response in an animal. In one embodiment, the present disclosure provides methods for the prevention and treatment of inflammatory bowel diseases, such as Crohn's disease. The methods comprise the administration of an immunologically effective amount of LpfA antigen to a subject in need thereof to immunize the subject against a pathogenic E. coli infection.

In one embodiment, the present disclosure provides methods for the prevention or treatment of mastitis by administering an effective amount of LpfA polypeptide sufficient to elicit an immune response in an animal. Mastitis is one of the most important production and welfare diseases affecting dairy cows. In recent decades, coliform infections have been identified in an ever increasing proportion of mastitis cases. Among the coliform bacteria E. coli is the dominant pathogenic species in dairy cow mastitis. The typical infection pattern for E. coli intramammary infection includes a clinically severe inflammatory response by the host with outcomes of either elimination of coliforms within 96 h of the initial infection or a deleterious outcome for the host including shock, sepsis and often death. In addition to severe disease several authors have reported persistent and clinically less severe E. coli infection.

In one embodiment, the present disclosure provides methods for the prevention or treatment of metritis by administering an effective amount of LpfA polypeptide sufficient to elicit an immune response in an animal. Ascending infection of the female genital tract with a wide range of bacteria occurs in almost all cattle after parturition. This infection often leads to disease of the upper female genital tract, which can be called pelvic inflammatory disease or metritis. Indeed, about 40% of animals develop PID within a week of parturition, and ~20% have endometritis that persists for >3 weeks. Infection of the endometrium with Gram-negative E. coli is the first step in the disease process for developing PID in cattle, preceding infection by the other bacteria such as Arcanobacterium pyogenes. The presence of E. coli is associated with the acute phase protein response, the severity of PID and the extent of the infertility.

In Vitro Diagnostic Methods

In one aspect, the disclosure provides an in vitro method for measuring the presence or absence of a LpfA nucleic acid or polypeptide in a sample from a subject. Comparisons may be made between the measured level of the LpfA nucleic acid or polypeptide in the subject to a reference level to diagnose a microbial infection or related condition.

Association between a pathological state (e.g., a microbial infection) and the aberration of the level of LpfA can be readily determined by comparative analysis in a normal population and an abnormal or affected population. Thus, for example, one can study the level of LpfA in both a normal population and a population affected with a particular pathological state. The study results can be compared and analyzed by statistical means. Any detected statistically significant difference in the two populations would indicate an association. For example, if the LpfA is statistically significantly higher in the affected population than in the normal population, then it can be reasonably concluded that higher LpfA is associated with the pathological state.

Statistical methods can be used to set thresholds for determining when the LpfA level in a subject can be considered to be different than or similar to a reference level. In addition, statistics can be used to determine the validity of the difference or similarity observed between a patient's LpfA level and the reference level. Useful statistical analysis methods are described in L. D. Fisher & G vanBelle, *Biostatistics: A Methodology for the Health Sciences* (Wiley-Interscience, NY, 1993). For instance, confidence ("p") values can be calculated using an unpaired 2-tailed t test, with a difference between groups deemed significant if the p value is less than or equal to 0.05. As used herein a "confidence interval" or "CI" refers to a measure of the precision of an estimated or calculated value. The interval represents the range of values, consistent with the data that is believed to encompass the "true" value with high probability (usually 95%). The confidence interval is expressed in the same units as the estimate or calculated value. Wider intervals indicate lower precision; narrow intervals indicate greater precision. Suitable confidence intervals are 90%, 95%, 97.5%, 98%, 99%, 99.5%, 99.9% and 99.99%. A "p-value" as used herein refers to a measure of probability that a difference between groups happened by chance. For example, a difference between two groups having a p-value of 0.01 (or p=0.01) means that there is a 1 in 100 chance the result occurred by chance. Suitable p values are 0.1, 0.05, 0.025, 0.02, 0.01, 0.005, 0.001, and 0.0001. Confidence intervals and p-values can be determined by methods well-known in the art. See, e.g., Dowdy and Wearden, *Statistics for Research*, John Wiley & Sons, New York, 1983.

Once an association is established between an aberrant LpfA level and a pathological state, then the particular physiological state can be diagnosed or detected by determining whether a patient has the particular aberration, i.e. elevated or reduced LpfA levels. The term "elevated levels" or "higher levels" as used herein refers to levels of LpfA that are higher than what would normally be observed in a comparable sample from control or normal subjects (i.e., a reference value). In some embodiments, "control levels" (i.e., normal levels) refer to a range of LpfA levels that would normally be expected to be observed in a mammal that does not have a microbial infection or an condition associated with a microbial infection. A control level may be used as a reference level for comparative purposes. "Elevated levels" refer to LpfA levels that are above the range of control levels. The ranges accepted as "elevated levels" or "control levels" are dependent on a number of factors. For example, one laboratory may routinely determine the level of LpfA in a sample that are different than the level of LpfA obtained for the same sample by another laboratory. Also, different assay methods may achieve different value ranges. Value ranges may also differ in various sample types, for example, different body samples or by different treatments of the sample. One of ordinary skill in the art is capable of considering the relevant factors and establishing appropriate reference ranges for "control values" and "elevated values". For example, a series of samples from control subjects and subjects diagnosed with iron disorders can be used to establish ranges that are "normal" or "control" levels and ranges that are "elevated" or "higher" than the control range.

Similarly, "reduced levels" or "lower levels" as used herein refer to levels of LpfA that are lower than what would normally be observed in a comparable sample from control or normal subjects (i.e., a reference value). In some embodiments, "control levels" (i.e. normal levels) refer to a range of LpfA levels that would normally be expected to be observed in a mammal that does not have a microbial infection and "reduced levels" refer to LpfA levels that are below the range of such control levels.

The methods and compositions described herein may be used to detect nucleic acids associated with various genes using a biological sample obtained from an individual. The nucleic acid (DNA or RNA) may be isolated from the sample according to any methods well known to those of skill in the art. Biological samples may be obtained by standard procedures and may be used immediately or stored, under conditions appropriate for the type of biological sample, for later use.

Starting material for the detection assays is typically a clinical sample, which is suspected to contain the target nucleic acids. An example of a clinical sample is a tissue of a subject having or suspected of having a microbial infection. Next, the nucleic acids may be separated from proteins and sugars present in the original sample. Any purification methods known in the art may be used in the context of the present invention. Nucleic acid sequences in the sample can successfully be amplified using in vitro amplification, such as PCR. Typically, any compounds that may inhibit polymerases are removed from the nucleic acids.

Methods of obtaining test samples are well known to those of skill in the art and include, but are not limited to, aspirations, tissue sections, swabs, drawing of blood or other fluids, surgical or needle biopsies, and the like. The test sample may be obtained from an individual or patient. For example, the test sample may contain cells, tissues or fluid obtained from a patient suspected of being afflicted with Crohn's disease, mastitis, or metritis. The test sample may be a cell-containing liquid or a tissue. Samples may include, but are not limited to, biopsies, blood, blood cells, bone marrow, fine needle biopsy samples, peritoneal fluid, amniotic fluid, plasma, pleural fluid, saliva, semen, serum, tissue or tissue homogenates, frozen or paraffin sections of tissue. Samples may also be processed, such as sectioning of tissues, fractionation, purification, or cellular organelle separation.

If necessary, the sample may be collected or concentrated by centrifugation and the like. The cells of the sample may be subjected to lysis, such as by treatments with enzymes, heat, surfactants, ultrasonication, or a combination thereof. The lysis treatment is performed in order to obtain a sufficient amount of nucleic acid derived from the cells in the sample to detect using polymerase chain reaction.

The nucleic acid to be amplified may be from a biological sample such as a tissue sample and the like. Various methods of extraction are suitable for isolating the DNA or RNA. Suitable methods include phenol and chloroform extraction. See Maniatis et al., *Molecular Cloning, A Laboratory Manual*, 2d, Cold Spring Harbor Laboratory Press, pp. 16-54 (1989). Buckingham and Flaws, *Molecular Diagnostics, Fundamentals, Methods & Clinical Applications*, F. A. Davis Co., pp. 65-70 (2007).

Nucleic acid samples or isolated nucleic acids may be amplified by various methods known to the skilled artisan. In a suitable embodiment, PCR is used to amplify nucleic acids of interest. Briefly, in PCR, two primer sequences are prepared that are complementary to regions on opposite complementary strands of the marker sequence. An excess of deoxynucleotide triphosphates are added to a reaction mixture along with a DNA polymerase, e.g., Taq polymerase.

The primers will bind to the sequence and the polymerase will cause the primers to be extended along the target sequence by adding on nucleotides. By raising and lowering the temperature of the reaction mixture, the extended primers will dissociate from the marker to form reaction products, excess primers will bind to the marker and to the reaction products and the process is repeated, thereby generating amplification products. Cycling parameters can be varied, depending on the length of the amplification products to be extended.

The skilled artisan is capable of designing and preparing primers that are appropriate for amplifying a target or marker sequence. The length of the amplification primers depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill. For example, the length of a short nucleic acid or oligonucleotide can relate to its hybridization specificity or selectivity. Exemplary primers for detecting LfpA genes are set forth in SEQ ID NOs: 5-8.

In some embodiments, the amplification may include a labeled primer or probe, thereby allowing detection of the amplification products corresponding to that primer or probe. In particular embodiments, the amplification may include a multiplicity of labeled primers or probes; such primers may be distinguishably labeled, allowing the simultaneous detection of multiple amplification products. In one embodiment, a primer or probe is labeled with a fluorogenic reporter dye that emits a detectable signal. While a suitable reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment, the detection reagent may be further labeled with a quencher dye such as Tamra, Dabcyl, or BLACK HOLE QUENCHER® (BHQ), especially when the reagent is used as a self-quenching probe such as a TAQMAN® (U.S. Pat. Nos. 5,210,015 and 5,538,848) or MOLECULAR BEACON® probe (U.S. Pat. Nos. 5,118,801 and 5,312,728), or other stemless or linear beacon probe (Livak et al., 1995, PCR Method Appl., 4:357-362; Tyagi et al, 1996, Nature Biotechnology, 14:303-308; Nazarenko et al., 1997, Nucl. Acids Res., 25:2516-2521; U.S. Pat. Nos. 5,866,336 and 6,117,635).

Nucleic acids may be amplified prior to detection or may be detected directly during an amplification step (i.e., "real-time" methods). In some embodiments, the target sequence is amplified using a labeled primer such that the resulting amplicon is detectably labeled. In some embodiments, the primer is fluorescently labeled. In some embodiments, the target sequence is amplified and the resulting amplicon is detected by electrophoresis.

In an illustrative embodiment, real time PCR is performed using TAQMAN® probes in combination with a suitable amplification/analyzer such as the ABI PRISM® 7900HT Sequence Detection System. The ABI PRISM® 7900HT Sequence Detection System is a high-throughput real-time PCR system that detects and quantitates nucleic acid sequences. Real time detection on the ABI PRISM 7900HT or 7900HT Sequence Detector monitors fluorescence and calculates Rn during each PCR cycle. The threshold cycle, or Ct value, is the cycle at which fluorescence intersects the threshold value. The threshold value is determined by the sequence detection system software or manually. The Ct can be correlated to the initial amount of nucleic acids or number of starting cells using a standard curve.

Oligonucleotide probes can be designed which are between about 10 and about 100 nucleotides in length and hybridize to the amplified region. Oligonucleotides probes are preferably 12 to 70 nucleotides; more preferably 15-60 nucleotides in length; and most preferably 15-25 nucleotides in length. The probe may be labeled. Amplified fragments may be detected using standard gel electrophoresis methods. For example, in some embodiments, amplified fractions are separated on an agarose gel and stained with ethidium bromide by methods known in the art to detect amplified fragments.

Targeting Agents for Peyer's Patches

The present inventors discovered that the LpfA polypeptides assist in trafficking across Peyer's patches. Accordingly, in one aspect, the disclosure provides methods for using the LpfA polypeptides as a targeting moiety to direct a bioactive agent or vaccine to Peyer's patches. Peyer's patches are aggregates of lymphoid nodules located in the wall of the small intestine, large intestine and appendix and are an important part of body's defense against the adherence and penetration of infectious agents and other substances foreign to the body. The immunologic response induced by the interaction of an antigen with the immune system may be either positive or negative with respect to the body's ability to mount an antibody or cell-mediated immune response to a subsequent reexposure to the antigen. While numerous antigens enter the body through the mucosal tissues, commonly employed immunization methods, such as intramuscular or subcutaneous injection of antigens or vaccines, rarely induce the appearance of sIgA antibodies in mucosal secretions. Secretory IgA antibodies are most effectively induced through direct immunization of the mucosally-associated lymphoid tissues, of which the Peyer's patches of the gastrointestinal tract represent the largest mass in the body.

Thus, in some embodiments, oral immunization may be used to induce protective antibodies. Extensive studies have demonstrated the feasibility of oral immunization to induce the common mucosal immune system, but with rare exception the large doses required to achieve effective immunization have made this approach impractical. It is apparent that any method or formulation involving oral administration of an ingredient be of such design that will target the delivery of the ingredient to the Peyer's patches. If not, the ingredient will reach the Peyer's patches, if at all, in an inadequate quantity.

As such, this disclosure relates to a method and formulation for targeting to and then releasing a bioactive agent in the body of an animal by mucosal application, and in particular, oral and intratracheal administration. In one embodiment, the agent is microencapsulated in a biocompatible polymer or copolymer, which is capable of passing through the gastrointestinal tract or existing on a mucosal surface without degradation or with minimal degradation so that the agent reaches and enters the Peyer's patches or other mucosally-associated lymphoid tissues unaltered and in effective amounts. The term biocompatible is defined as a polymeric material which is not toxic to the body, is not carcinogenic, and which should not induce inflammation in body tissues.

In one embodiment, nano- and microparticles that are loaded with, or encapsulate, pharmaceutical agents, can be coated with the polypeptide ligands, such as the LpfA polypeptides of the present invention, that target intestinal epithelium tissue, such as M-cell or Peyer's patch tissue. The coating can be effected by covalent or non-covalent bonding. The covalent bonding can be achieved by adsorption or any other coating process. In either case, the bonding can be made to completed particles or to particle components that subsequently form part of the particles.

Pharmaceutical agents can, in the alternative, be directly linked to LpfA polypeptide ligands. If the agent is itself a polypeptide or peptide, the product is a chimeric polypeptide comprising both an agent and a targeting portion. Bacterial vectors can express a targeting ligand on their surface and also express an antigen on their surface or carry a gene coding for the antigen or other therapeutic agent. Viral vectors can express a targeting ligand on their surface and also express an antigen on their surface or carry a gene coding for the antigen.

A "pharmaceutical agent" or "bioactive agent" is a therapeutic or diagnostic agent. Therapeutic agents are those that are administered either to treat an existing disease or prophylactically to protect against a potential future disease. Diagnostic agents are any agents that are administered as part of a diagnostic procedure. Examples of therapeutic agents are drugs, genes, gene-delivery vectors, DNA vaccines, antigens and recombinant viruses. Drugs include, for example, analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, anti-neoplastics, prostaglandins and antidiuretic agents, antisense oligonucleotides, gene-correcting hybrid oligonucleotides, ribozymes, RNA interference (RNA.sub.i) oligonucleotides, silencing RNA (siRNA) oligonucleotides, aptameric oligonucleotides and triple-helix forming oligonucleotides. Examples of gene-delivery vectors are DNA molecules, viral vectors (e.g. adenovirus, adeno-associated virus, retroviruses, herpes simplex virus, and sindbus virus), and cationic lipid-coated DNA and DNA-dendrimers. Examples of antigens that are therapeutic agents are tumor antigens, pathogen antigens and allergen antigens. A vaccine preparation will contain at least one antigen. "Pathogen antigens" are those characteristic of pathogens, such as antigens derived from viruses, bacteria, parasites or fungi.

Adjuvants can, if desired, be delivered by the carrier entity or with a carrier entity. Examples of adjuvants are Freund's Complete Adjuvant, Freund's Incomplete Adjuvant, Hunter's Titermax, Gerbu Adjuvant, Ribi's Adjuvant, Montanide ISA Adjuvant, Aluminum Salt Adjuvants and Nitrocellulose adsorbed protein.

A suitable method of the invention for administering a carrier entity to a subject having intestinal epithelium comprises contacting the intestinal epithelium with a LpfA polypeptide ligand of the invention in the presence of the carrier entity, such that the carrier entity is transported into or across the intestinal epithelium or into or across a region of the intestine such as M-cells or Peyer's patches. The carrier entity and the polypeptide ligand can be administered together (e.g., as part of an entity-ligand complex or discretely) or separately. Oral administration is suitable, but other modes of administration requiring transepithelial transport to reach the target tissue are also acceptable (e.g., rectal administration). The ability of the LpfA polypeptides to target certain cells of the intestinal epithelium also makes the ligands suitable for targeting pharmaceutical agents to the cells themselves for therapy or prophylaxis.

Dosage and Formulation of Pharmaceutical Compositions

The present invention envisions treating a disease, for example, *E. coli*-related diseases, infections and the like, in a mammal by the administration of the compositions of the present invention. Administration of the vaccines may be continuous or intermittent, depending, for example, upon the recipient's physiological condition, whether the purpose of the administration is therapeutic or prophylactic, and other factors known to skilled practitioners. The administration of the vaccines of the invention may be essentially continuous over a preselected period of time or may be in a series of spaced doses. Both local and systemic administration is contemplated.

In one embodiment, the LpfA polypeptides are administered directly to a subject to achieve the desired immune response. In another embodiment, immune cells from a subject are contacted with the LpfA polypeptides ex vivo and then re-administered to the subject to achieve the desired immune response. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

Typically, an effective amount of the compositions of the present invention, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. For administration of LpfA polypeptides, the dosage ranges from about 0.0001 to 100 mg/kg, and more usually 0.01 to 5 mg/kg every week, every two weeks or every three weeks, of the subject body weight. For example dosages can be 1 mg/kg body weight or 10 mg/kg body weight every week, every two weeks or every three weeks or within the range of 1-10 mg/kg every week, every two weeks or every three weeks.

The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the patient can be administered a prophylactic regime.

One or more suitable unit dosage forms having the compositions of the invention, which, as discussed below, may optionally be formulated for sustained release (for example using microencapsulation, see WO 94/07529, and U.S. Pat. No. 4,962,091), can be administered by a variety of routes including parenteral, including by intravenous and intramuscular routes, as well as by direct injection into the diseased tissue. For example, the vaccine may be directly injected into a tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the compositions are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes. The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The compositions of the present invention may also comprise nucleic acids encoding the LpfA polypeptides or bioactive agent. Pharmaceutical formulations, dosages and routes of administration for nucleic acids are generally disclosed, for example, in Feigner et al., 1987, *PNAS* 84: 7413-7417. In one embodiment nucleic acids are administered directly to a patient, e.g., to the site of the tumor or using a combination of one or more targeting agents to target the nucleic acid to an immune cell. In another embodiment, nucleic acids are contacted with immune cells isolated from the subject, and the transfected cells are introduced into the patient. The nucleic acid molecule encoding the fusion protein of the present invention may be operatively linked to essential genetic regulatory elements, such as a promoter, an enhancer, a selection marker, and the like.

Adjuvants.

In some embodiments, the LpfA polypeptide of the present invention is administered with an adjuvant. Immunization protocols often use adjuvants to stimulate immune responses. Some adjuvants affect the way in which antigens are presented. For example, the immune response is increased when protein antigens are precipitated by alum. Emulsification of antigens also prolongs the duration of antigen presentation. Other adjuvants, for example, certain organic molecules obtained from bacteria, act on the subject rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen. In order to reinforce the immunological effect of the LpfA polypeptides of the present invention, the pharmaceutical composition can comprise an immunologic adjuvant, such as complete/incomplete Freund's adjuvant, alum, calcium phosphate, oligodeoxyribonucleotide, as well as cytokines, e.g. IL-2, 4, 12, 15, interferon α, γ, granulocyte-macrophage colony stimulating factor and the like.

EXAMPLES

Example 1

Genes with Homology to LpfA are Common in *E. coli* Strains Isolated from Human Ileum Microarray Analysis of Virulence Determinants.

A comprehensive screening of virulence genes of 22 *E. coli* strains isolated from the ileum of 13 patients with Crohn's ileitis and 9 with a healthy ileum (7 colonic Crohn's disease, 2 healthy people), was conducted using the DNA microarray developed by Bruant et al. (*Appl Environ Microbiol.* 2006 May; 72(5):3780-4). This microarray contains 251 oligonucleotide probes specific for 183 virulence genes or markers representative of all known *E. coli* pathotypes. These probes are specific for various virulence genes, including genes encoding adhesins, toxins, hemolysins, invasins, autotransporters, capsular, flagellar, and somatic antigens, iron acquisition system or transport proteins, and outer membrane proteins, as well as genes recently shown to be associated with virulence in *E. coli*.

Briefly, DNA from *E. coli* strains were fluorescently labeled with a Cy5 dye and with a random-priming protocol derived from the BIOPRIME® DNA labeling system (Invitrogen Life Technologies). Microarrays were then hybridized overnight in the dark with 500 ng of labeled DNA, in a slide hybridization chamber (Corning Canada). After hybridization, the microarrays were scanned with a ScanArray Lite fluorescent microarray analysis system (Canberra-Packard Canada). All microarray hybridizations were performed in duplicate, with DNA obtained from two separate bacterial culture.

The results of the microarray analysis showed that 8 out of 13 ICD strains (61.5%) hybridized to nucleotides for LpfA. Seven ICD strains had the 154 variant and one ICD strain had the 141 variant. Five out of nine healthy ileum strains (CCD+ healthy) (55.5%) were positive for LpfA. Four of the positive LpfA strains had the 154 variant and one had both 154 and 141.

Subsequent PCR analysis was performed on the initial 22 ileal *E. coli* strains (i.e., those analyzed by microarray) and an additional 26 *E. coli* strains isolated from ileal biopsies. PCR-based analysis of our collection of 48 ileal associated *E. coli* (25 ICD and 23 healthy ileum) showed that Lpf 154 was present in 21 strains; Lpf 141 was positive in 9 strains; and both 154 and 141 were detected in 7 strains. LpfA was more prevalent among strains from inflamed (56%) than healthy ileum (39%). As such, methods for detecting Lpf 154 and/or 141 in samples from a subject are useful for the diagnosis of Crohn's ileitis.

Example 2

Invasion of Cultured Intestinal Epithelial Cells by *E. coli* Strains Isolated from Human Ileum is Related to the Presence of Genes with Homology to LpfA The invasive abilities of *E. coli* isolates were evaluated in cultured epithelial cells by the gentamicin protection assay. Caco-2 cells were grown in 24-well plates for 7 days (~5× $10^6$) and infected with *E. coli* strains at an multiplicity of infection (MOI) of 20 for 3 h. Intracellular bacteria were determined as described previously (Simpson et al., *Infect Immun.* 2006 August; 74(8):4778-92). Each assay was run in duplicate and repeated at least three times. Invasion was expressed as the total number of CFU/ml recovered per well. A non-invasive *E. coli* strain DH5α and *E. coli* strain LF82, a strain isolated from a patient with ICD in France that displays adherent and invasive behavior in cultured cells, were used as negative and positive controls, respectively.

A statistically significant relationship was found between the presence of sequences with homology to LpfA on microarray and epithelial cell invasion (p=0.024): median invasion log cfu/ml for LpfA positive strains was 3.5 vs. 2.15 for LpfA negative strains. The relationship between the presence of LpfA and epithelial cell invasion in the expanded strain collection (43 strains were evaluated in invasion experiments) was statistically significant p=0.029 (Mann Whitney): median invasion log cfu/ml for LpfA positive strains was 3.4 vs. 2.2 for LpfA negative strains. Thus, *E. coli* containing these LpfA genes are capable of invading cultured epithelial cells.

Example 3

LpfA Sequencing, Phylogenetic Tree Construction and Similarity Value Determination The whole LpfA coding region was amplified with primers specific for lpfA 154 (lpfA154-F: GCC GTC TCT TTG GTG TAC TAT TCC (SEQ ID NO: 5) and lpfA154-R: CCA CCA ATG ACA ACG CCT GCA TAA (SEQ ID NO: 6)) and lpfA 141 (lpfA141 F: GCA CCA TTT GTA TAA TCT GCG CCC (SEQ ID NO: 7) and lpfA141 R: TGA GAG ATG ATC GTT CCG TCA GGA (SEQ ID NO: 8)). Column purified PCR amplicons were sequenced at the Cornell University BioResource Center, using forward and reverse PCR primers and an ABI 3700 automated DNA sequencer and ABI PRISM Big-Dye Terminator Sequencing kits with AmpliTaq DNA Polymerase (Applied Biosystems, Foster City, Calif., USA). DNA sequences obtained with both forward and reverse primers were proofread, and then assembled in SeqMan (DNAStar, Madison, Wis., USA). Sequences were aligned using the Clustal-W algorithm. A neighbour-joining tree with Jukes Cantor corrections was constructed in MEGA 4 software. Bootstrap values were calculated from 1000 replicate analyses. Reference sequences included in the phylogenetic tree were downloaded from NCBI. For similarity values, lpfA sequences were examined by BLASTN (NCBI, Bethesda Md.) against known lpfA sequences.

Figure 2:
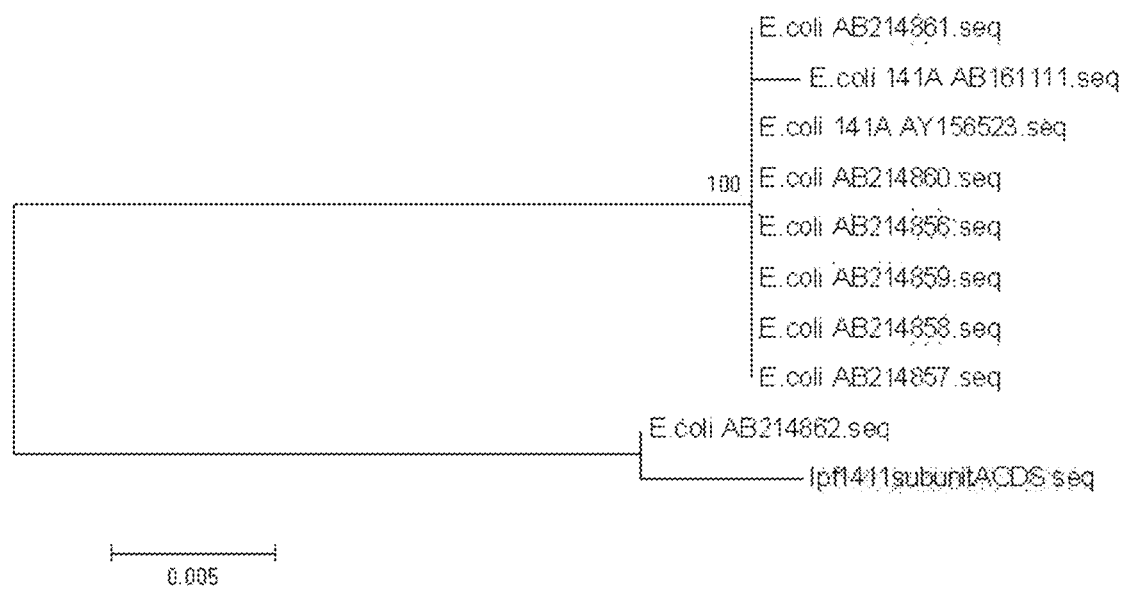
FIG. 2 is a dendrogram showing the alignment of LpfA 141 subunit detected in ileal CD isolate LF82 and other ileal strains.

The nucleotide sequences of LpfA variants 154 (SEQ ID NO: 1) and 141 (SEQ ID NO: 3) present in two ileitis-associated strains (541-15 and LF82) are shown in Tables 1 and 3 above. The relationship of these sequences to others in the database is shown in the dendrograms in FIGS. 1 and 2. FIG. 1 is a dendrogram showing the alignment of the LpfA subunit present in Crohn's ileitis-associated strain 541-15. Highest homology to LpfA 154 and stg fimbrial subunit A. FIG. 2 is a dendrogram showing the alignment of LpfA 141 subunit detected in ileal CD isolate LF82 and other ileal strains.

Example 4

Deletion of LpfA Decreases Translocation Across M Cells and CACO-2 Cells

To examine the impact of LpfA subunit on the trafficking of *E. coli* across Peyer's patches, deletion mutants of LpfA subunit of Lpf154 were created using homologous recombination and lambda red transformed AIEC 541-15 and MT-8. LpfA 154 deletion mutants of ileal-derived adherent and invasive E. coli strains were significantly impaired in their ability to translocate across M cells (P<0.05). LpfA 154 deletion mutants of strain MT-8 were also less able to translocate across CACO-2 cells, as shown in Table 5 below. These results indicate that LpfA 154 is an important virulence factor in trafficking of E. coli across Peyer's patches.

TABLE 5

LpfA Deletion Analysis

| Translocation (cfu/ml) | CUMT8 wild type | CUMT8 LpfA deletion | 541-15 wild type | 541-15 deletion |
|---|---|---|---|---|
| M-cell | *1113 ± 483 | 323 ± 207 | 350 ± 259 | 111 ± 55 |
|  | *6392 ± 938 | 2324 + 556 | *3024 + 319 | 1157 ± 81 |
| Caco-2-cl1 cell | 214 + 94 | 20 ± 20 | 195 ± 97 | 163 ± 53 |
|  | 811 ± 170 | 437 ± 34 | 534 ± 170 | 630 ± 183 |

Example 5

Genes with Homology to LpfA are Common in E. coli Strains Isolated from Bovine Mastitic Milk and Uterus of Cows with Endometritis PCR analysis was performed on E. coli strains isolated from bovine mastitic milk and uterus of cows with endometritis. Fourteen out of twenty-eight bovine mastitis strains (50%) were positive for LpfA. Five of the positive LpfA strains had the 154 variant, two had the 141 variant, and seven had both 154 and 141. Twenty-six out of thirty-six bovine metritis strains (72%) were positive for LpfA. Fifteen of the positive LpfA strains had the 154 variant, one had the 141 variant, and ten had both 154 and 141.

Figure 4:
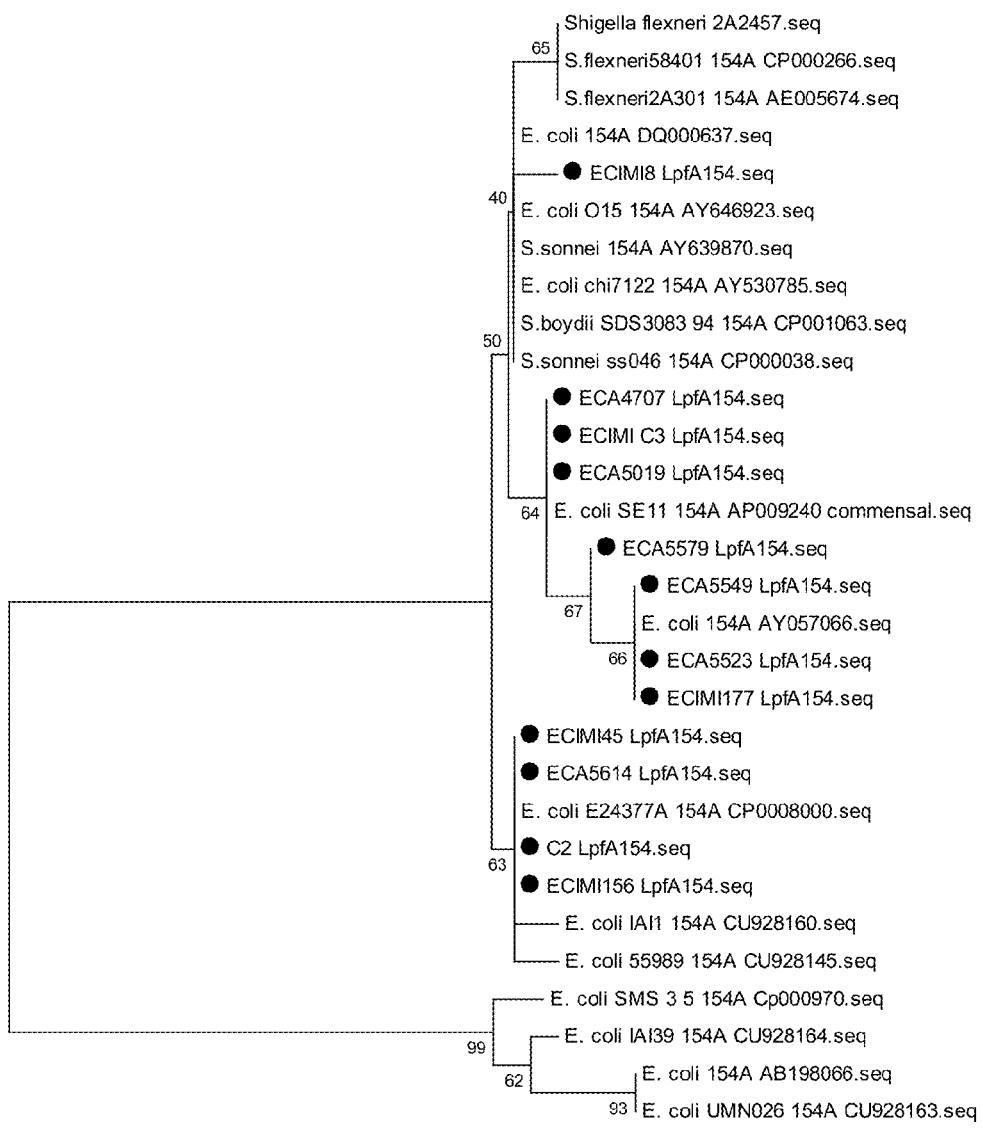
FIG. 4 is a dendrogram showing the alignment of the LpfA 154 subunit detected in mastitis *E. coli* isolates.
Figure 5:
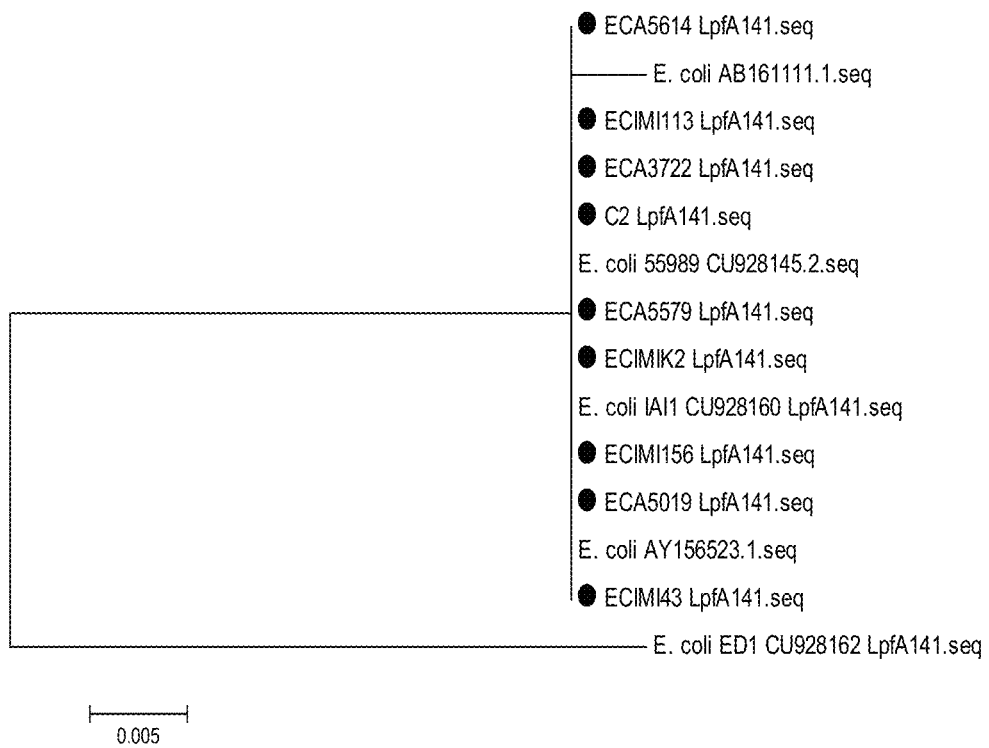
FIG. 5 is a dendrogram showing the alignment of the LpfA 141 subunit detected in mastitis *E. coli* isolates.

The nucleotide sequences of the LpfA genes from the E. coli isolates was determined as described above. FIG. 4 is a dendrogram showing the alignment of the LpfA 154 subunit detected in mastitis E. coli isolates. FIG. 5 is a dendrogram showing the alignment of the LpfA 141 subunit detected in mastitis E. coli isolates.

The invasive abilities of E. coli isolates were evaluated in cultured epithelial cells by the gentamicin protection assay. A bovine mammary epithelial cell line, MAC-T (Nexia Biotechnologies, Step-Anne de Bellevue, Que, Canada) was used. Monolayers of MAC-T cells were kept at 37° C. in 5% $CO_2$:95% air (vol/vol) using Dulbecco's Modified Eagle's Medium (DMEM, Sigma-Aldrich, St. Louis, Mo.) supplemented with 5% fetal bovine serum (FBS, Gemini Bio Products, Woodland, Calif.). E. coli strains were grown in LB overnight and stationary-phase bacteria were pelleted, washed with excess PBS, pH 7.4, and resuspended in PBS. Confluent monolayers of MAC-T cells (~$3.5 \times 10^5$) grown in 24-well plates were infected with a multiplicity of infection of 20. After 1 h of incubation at 37° C. with 5% $CO_2$, cells were washed three times in PBS and then incubated for another 2 h with medium containing 100 µg/ml gentamicin (Sigma-Aldrich, St. Louis, Mo.) to kill any extracellular bacteria. After 2 h cells were lysed with 1 ml of 0.1% Triton X-100 in PBS for 10 min. Lysates were serially diluted and plated on LB-agar, and colonies were enumerated following overnight incubation. The number of bacteria in each well was determined as described above and invasion was expressed as the total number of CFU/ml recovered per well.

Figure 3:
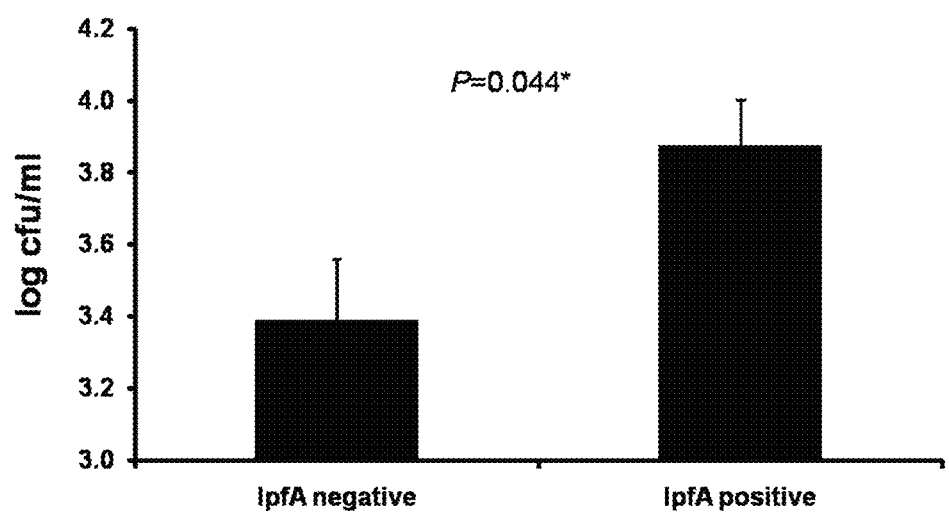
FIG. 3 is a chart showing the effect of long polar fimbriae on MAC-T cell invasion.

The results are shown in FIG. 3 and indicate that E. coli strains containing LpfA are more effective at invading MAC-T cells than strains lacking this gene.

Example 6

Therapeutic and Prophylactic Vaccination of Human Subjects (Prophetic)

The LpfA polypeptides of the present invention can be used in treatment of microbial infections and diseases caused thereby. Specifically, the invention provides for both prophylactic and therapeutic methods of treating a subject at risk of (or susceptible to) a disorder or having a disorder associated with an E. coli infection. Administration of a prophylactic LpfA polypeptide can occur prior to the manifestation of symptoms characteristic of the infection, such that a disease or condition is prevented or, alternatively, delayed in its progression. In therapeutic applications, LpfA polypeptides of the present invention are administered to a subject suspected of, or already suffering from, an E. coli infection. An amount adequate to accomplish therapeutic or prophylactic treatment is defined as a therapeutically- or prophylactically-effective dose.

In this Example, human subjects having an E. coli-related disease, e.g. Crohn's ileitis, are administered the vaccine compositions of the present invention. A vaccine comprising the polypeptide of SEQ ID NO: 2 and/or 4 is administered to a human subject having or at risk for having an infectious disease associated with pathogenic E. coli. After treatment, patient condition is monitored for occurrence of the symptoms of infection. A successful treatment using the vaccine compositions of the invention is characterized by the prevention or delay in the onset of symptoms of Crohn's ileitis or a reduction in the symptoms of Crohn's ileitis in the subject compared to a normal subject (i.e., one without microbial infection).

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, issued patents, and other documents referred to in the present disclosure are herein incorporated by reference as if each individual publication, patent application, issued patent, or other document were specifically and individually indicated to be incorporated by reference in its entirety. Definitions that are contained in text incorporated by reference are excluded to the extent that they contradict definitions in this disclosure.

What is claimed is:

1. A composition comprising an immunologically effective amount of an isolated *Escherichia coli* (*E. coli*) Long polar fimbriae subunit A (LpfA) antigen and an effective amount of an agent selected from the group consisting of, a stabilizing agent, a solubilizing agent, and an emulsifying agent, wherein the LpfA antigen is the polypeptide of SEQ ID NO: 2 or SEQ ID NO: 4.

2. The composition of claim 1 further comprising an adjuvant.

3. A method of eliciting an immune response in an animal subject, the method comprising administering to the subject an effective amount of the composition of claim 1.

4. The method of claim 3, wherein the immune response provides prophylaxis against a microbial infection caused by a pathogenic *E. coli*.

5. The method of claim 4, wherein the microbial infection results in a condition selected from the group consisting of: Crohn's disease, mastitis and metritis.

6. The method of claim 3, wherein the administration is oral, intradermal, intramuscular, intraperitoneal, intravenous, subcutaneous, or intranasal.

7. A composition comprising an isolated LpfA polypeptide of SEQ ID NO: 2 or SEQ ID NO: 4 and a carrier entity selected from the group consisting of a nanoparticle, a microparticle, a liposome, a bacteria, a phage, and a viral carrier, wherein the carrier entity is associated with a bioactive agent, and wherein the polypeptide is covalently or non-covalently bound to a carrier entity.

8. The composition of claim 7, wherein the carrier entity is a nanoparticle, microparticle, or liposome, and wherein the nanoparticle, microparticle, or liposome is loaded with the bioactive agent or encapsulated with the bioactive agent.

9. The composition of claim 8, wherein the bioactive agent is a vaccine.

10. A method of eliciting an immune response in an animal subject comprising administering the composition of claim 7.

11. The method of claim 10, wherein the subject is a mammal.

12. The method of claim 11, wherein the mammal is a human.

13. The method of claim 10, wherein the administration is via the oral, rectal, subcutaneous, intramuscular, nasal, or intravenous route.

14. The method of claim 10, wherein the composition contacts the intestinal epithelium of the subject.

* * * * *

SEQUENCE LISTING

<160> NUMBER OF SEQ ID NOS: 8

<210> SEQ ID NO 1
<211> LENGTH: 570
<212> TYPE: DNA
<213> ORGANISM: Escherichia coli

<400> SEQUENCE: 1

```
atgaagcgta atattatagg cggtgcattc actctggcat ctctaatgct ggccgggcat      60
gcactggcag aagatggtgt tgttcacttc gtcggtgaaa ttgtcgacac tacttgtgaa     120
gttacctccg atacagccga tcaaattgtc ccactgggta aagtcagtaa aaatgcattt     180
tcaggtgtag gtagtctggc gtcgccacag aagttcagta ttaagcttga aaattgcccg     240
gcaacgtaca ctcaagcagc cgttcgtttt gatggtacag aagcgcctgg cggcgacggc     300
gacctgaaag tgggtacgcc gcttacagca ggcaaccctg gtgattttac cggtacagga     360
caagcgattg cggcaaccgg cgttggtatt cgtatttta accagtccga taattcgcag     420
gttaaacttt ataacgactc tgcttatacc gctatcgatg ctgaaggcaa ggctgaaatg     480
aagtttattg cacgctatgt ggcaaccaat gcgaccgtaa cggctggtac ggcgaacgcg     540
gattcacaat ttactgtcga atataagaaa                                      570
```

<210> SEQ ID NO 2
<211> LENGTH: 190
<212> TYPE: PRT
<213> ORGANISM: Escherichia coli

<400> SEQUENCE: 2

```
Met Lys Arg Asn Ile Ile Gly Gly Ala Phe Thr Leu Ala Ser Leu Met
1               5                   10                  15

Leu Ala Gly His Ala Leu Ala Glu Asp Gly Val Val His Phe Val Gly
            20                  25                  30

Glu Ile Val Asp Thr Thr Cys Glu Val Thr Ser Asp Thr Ala Asp Gln
        35                  40                  45

Ile Val Pro Leu Gly Lys Val Ser Lys Asn Ala Phe Ser Gly Val Gly
    50                  55                  60

Ser Leu Ala Ser Pro Gln Lys Phe Ser Ile Lys Leu Glu Asn Cys Pro
65                  70                  75                  80

Ala Thr Tyr Thr Gln Ala Ala Val Arg Phe Asp Gly Thr Glu Ala Pro
                85                  90                  95

Gly Gly Asp Gly Asp Leu Lys Val Gly Thr Pro Leu Thr Ala Gly Asn
            100                 105                 110

Pro Gly Asp Phe Thr Gly Thr Gly Gln Ala Ile Ala Ala Thr Gly Val
        115                 120                 125

Gly Ile Arg Ile Phe Asn Gln Ser Asp Asn Ser Gln Val Lys Leu Tyr
    130                 135                 140

Asn Asp Ser Ala Tyr Thr Ala Ile Asp Ala Glu Gly Lys Ala Glu Met
145                 150                 155                 160
```

```
Lys Phe Ile Ala Arg Tyr Val Ala Thr Asn Ala Thr Val Thr Ala Gly
                165                 170                 175

Thr Ala Asn Ala Asp Ser Gln Phe Thr Val Glu Tyr Lys Lys
            180                 185                 190

<210> SEQ ID NO 3
<211> LENGTH: 525
<212> TYPE: DNA
<213> ORGANISM: Escherichia coli

<400> SEQUENCE: 3
atgaaaaagg ttctgtttgc cttatctgcg cttgcgctga cctctacttc cgtattcgca    60
gctgatgcag gcgacggttc tgttaaattc accggagaga ttgttgacgc cgcttgtgtt   120
gtgtctccag acactcaaaa acaagaagtt gttctgggcc aggtgaacaa gtctgtgttt   180
accactactg gtgataaatc tgcagcaact ccgttcaaaa ttaaactgga aaactgcgat   240
atctccactt tcaaaaatgt ggagatcagc tttaacggtg ttggcgacgc agacaacagc   300
aaactgattt ctgtaagcac tgaaccaggt gccgcaactg gcgtgggtat tggtatttat   360
gataatacca atacgctggt tgatctgaat accggtaaat ctgctaccgt cctgaaagaa   420
ggccagactg ttctgtattt taccgctaac tatgtcgcta ccaaaaatgc agtaaccatc   480
ggttacggta atgccgaagt cgacttcaac ctgacttaca actaa                   525

<210> SEQ ID NO 4
<211> LENGTH: 174
<212> TYPE: PRT
<213> ORGANISM: Escherichia coli

<400> SEQUENCE: 4

Met Lys Lys Val Leu Phe Ala Leu Ser Ala Leu Ala Leu Thr Ser Thr
1               5                  10                  15

Ser Val Phe Ala Ala Asp Ala Gly Asp Gly Ser Val Lys Phe Thr Gly
            20                  25                  30

Glu Ile Val Asp Ala Ala Cys Val Val Ser Pro Asp Thr Gln Lys Gln
        35                  40                  45

Glu Val Val Leu Gly Gln Val Asn Lys Ser Val Phe Thr Thr Thr Gly
    50                  55                  60

Asp Lys Ser Ala Ala Thr Pro Phe Lys Ile Lys Leu Glu Asn Cys Asp
65                  70                  75                  80

Ile Ser Thr Phe Lys Asn Val Glu Ile Ser Phe Asn Gly Val Gly Asp
                85                  90                  95

Ala Asp Asn Ser Lys Leu Ile Ser Val Ser Thr Glu Pro Gly Ala Ala
            100                 105                 110

Thr Gly Val Gly Ile Gly Ile Tyr Asp Asn Thr Asn Thr Leu Val Asp
        115                 120                 125

Leu Asn Thr Gly Lys Ser Ala Thr Val Leu Lys Glu Gly Gln Thr Val
    130                 135                 140

Leu Tyr Phe Thr Ala Asn Tyr Val Ala Thr Lys Asn Ala Val Thr Ile
145                 150                 155                 160

Gly Tyr Gly Asn Ala Glu Val Asp Phe Asn Leu Thr Tyr Asn
                165                 170

<210> SEQ ID NO 5
<211> LENGTH: 24
<212> TYPE: DNA
<213> ORGANISM: Artificial sequence
```

```
<220> FEATURE:
<223> OTHER INFORMATION: Synthetic primer

<400> SEQUENCE: 5
gccgtctctt tggtgtacta ttcc                                              24

<210> SEQ ID NO 6
<211> LENGTH: 24
<212> TYPE: DNA
<213> ORGANISM: Artificial sequence
<220> FEATURE:
<223> OTHER INFORMATION: Synthetic primer

<400> SEQUENCE: 6
ccaccaatga caacgcctgc ataa                                              24

<210> SEQ ID NO 7
<211> LENGTH: 24
<212> TYPE: DNA
<213> ORGANISM: Artificial sequence
<220> FEATURE:
<223> OTHER INFORMATION: Synthetic primer

<400> SEQUENCE: 7
gcaccatttg tataatctgc gccc                                              24

<210> SEQ ID NO 8
<211> LENGTH: 18
<212> TYPE: DNA
<213> ORGANISM: Artificial sequence
<220> FEATURE:
<223> OTHER INFORMATION: Synthetic primer

<400> SEQUENCE: 8
atgatcgttc cgtcagga                                                     18
```